(12) United States Patent
Dix et al.

(10) Patent No.: US 8,710,004 B2
(45) Date of Patent: *Apr. 29, 2014

(54) STABLE LIQUID VEGF ANTAGONIST FORMULATIONS

(75) Inventors: Daniel Dix, LaGrangeville, NY (US); Kelly Frye, Mendham, NJ (US); Susan Kautz, Albany, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 34 days.

This patent is subject to a terminal disclaimer.

(21) Appl. No.: 13/428,510

(22) Filed: Mar. 23, 2012

(65) Prior Publication Data

US 2012/0178683 A1 Jul. 12, 2012

Related U.S. Application Data

(60) Continuation of application No. 13/343,214, filed on Jan. 4, 2012, now Pat. No. 8,404,638, which is a division of application No. 12/835,065, filed on Jul. 13, 2010, now Pat. No. 8,110,546, which is a continuation of application No. 11/387,256, filed on Mar. 22, 2006, now abandoned.

(60) Provisional application No. 60/665,125, filed on Mar. 25, 2005.

(51) Int. Cl.
*A61K 38/18* (2006.01)
*A61K 39/00* (2006.01)
*C12P 21/02* (2006.01)
*C07H 21/04* (2006.01)

(52) U.S. Cl.
USPC ... 514/8.1; 424/185.1; 424/192.1; 424/139.1; 435/69.7; 536/23.4

(58) Field of Classification Search
None
See application file for complete search history.

(56) References Cited

U.S. PATENT DOCUMENTS

| | | | |
|---|---|---|---|
| 5,399,670 A | 3/1995 | Bhattacharya et al. | |
| 5,763,401 A | 6/1998 | Nayar | |
| 5,851,999 A | 12/1998 | Ulrich et al. | |
| 6,011,003 A | 1/2000 | Charmock-Jonee | |
| 6,100,071 A | 8/2000 | Davis-Smyth et al. | |
| 6,267,958 B1 | 7/2001 | Andya et al. | |
| 6,270,993 B1 | 8/2001 | Shibuya | |
| 6,875,432 B2 | 4/2005 | Liu et al. | |
| 6,897,294 B2 | 5/2005 | Davis-Smyth et al. | |
| 7,001,892 B1 | 2/2006 | Chmielweski et al. | |
| 7,052,691 B2 | 5/2006 | Sleeman et al. | |
| 7,060,268 B2 | 6/2006 | Andya et al. | |
| 7,087,411 B2 | 8/2006 | Daly et al. | |
| 7,374,757 B2 | 5/2008 | Papadopoulos et al. | |
| 2003/0092606 A1 | 5/2003 | L'Italien et al. | |
| 2003/0113316 A1 | 6/2003 | Kaisheva et al. | |
| 2003/0202972 A1 | 10/2003 | Andya et al. | |
| 2004/0197324 A1 | 10/2004 | Liu et al. | |
| 2005/0032699 A1 | 2/2005 | Holash et al. | |
| 2005/0276808 A1 | 12/2005 | Cedarbaum | |
| 2005/0281831 A1 | 12/2005 | Davis-Smyth et al. | |

FOREIGN PATENT DOCUMENTS

| | | | | |
|---|---|---|---|---|
| WO | WO9300807 A1 | 1/1993 | | |
| WO | WO9913909 A1 | 3/1999 | | |
| WO | WO0075319 A1 | 12/2000 | | |
| WO | WO02060489 A1 | 8/2002 | | |
| WO | WO2004106378 A1 | 12/2004 | | |
| WO | WO2005000895 A1 | 1/2005 | | |
| WO | WO2005020972 A1 | 3/2005 | | |
| WO | WO2005072772 | * | 8/2005 | ........... A61K 39/395 |
| WO | WO2006047325 A1 | 5/2006 | | |
| WO | WO2007149334 A1 | 12/2007 | | |

OTHER PUBLICATIONS

Carpenter, J.F. (1997) Rational Design of Stable Lyophilized . . . , Pharm. Res. 14(8): 969-975.
Wang, W. (1999) Instability, stabilization, and formulation of liquid protein . . . , Int'l. J. Pharmaceutics 185(2): 129-188.
Webb et al. (2002) A new mechanism for decreasing aggregation . . . , J. Pharm. Sci. 91(2): 543-558.
Katayama et al. (2004) Retrospective statistical analysis of lyophilized . . . , J. Pharm. Sci. 93(10): 2609-2623.
Daugherty, et al. (2006) Formulation and delivery issues for monoclonal . . . , Adv. Drug Delivery Rev. 58:686-706.
Fraser et al. (2004) Single injections of Vascular Trap . . . , J. Clin. Endocrin. & Metabol. 90(2):1114-1122.
Hank's Solution http://www.lifetechnologies.com/us/en/home/technical-resources/media-formulation.152.html.

* cited by examiner

*Primary Examiner* — Elly-Gerald Stoica
(74) *Attorney, Agent, or Firm* — Joseph Zahner; Mary C. Johnson; Valeta Gregg

(57) ABSTRACT

Formulations of a vascular endothelial growth factor (VEGF)-specific fusion protein antagonist are provided including a pre-lyophilized formulation, a reconstituted lyophilized formulation, and a stable liquid formulation. Preferably, the fusion protein has the sequence of SEQ ID NO:4.

6 Claims, No Drawings

SEQUENCE LISTING

<160> NUMBER OF SEQ ID NOS: 4

<210> SEQ ID NO 1
<211> LENGTH: 1453
<212> TYPE: DNA
<213> ORGANISM: Artificial Sequence
<220> FEATURE:
<223> OTHER INFORMATION: Synthetic

<400> SEQUENCE: 1

```
aagcttgggc tgcaggtcga tcgactctag aggatcgatc cccgggcgag ctcgaattcg      60
caaccaccat ggtcagctac tgggacaccg gggtcctgct gtgcgcgctg ctcagctgtc     120
tgcttctcac aggatctagt tccggaggta gaccttctgt agagatgtac agtgaaatcc     180
ccgaaattat acacatgact gaaggaaggg agctcgtcat tccctgccgg gttacgtcac     240
ctaacatcac tgttacttta aaaaagtttc cacttgacac tttgatccct gatggaaaac     300
gcataatctg ggacagtaga aagggcttca tcatatcaaa tgcaacgtac aagaaatag     360 ggcttctgac ctgtgaagca acagtcaatg gcatttgta taagacaaac tatctcacac     420
atcgacaaac caatacaatc atagatgtgg ttctgagtcc gtctcatgga attgaactat     480
ctgttggaga aagcttgtc ttaaattgta gcaagaac tgaactaaat gtggggattg     540
acttcaactg ggaataccct tcttcgaagc atcagcataa gaaacttgta accgagacc     600 taaaaaccca gtctgggagt gagatgaaga aatttttgag caccttaact atagatggtg     660
taacccggag tgaccaagga ttgtacacct gtgcagcatc cagtgggctg atgaccaaga     720
agaacagcac atttgtcagg gtccatgaaa agggcccggg cgacaaaact cacacatgcc     780
caccgtgccc agcacctgaa ctcctggggg gaccgtcagt cttcctcttc ccccaaaac     840 ccaaggacac cctcatgatc tcccggaccc ctgaggtcac atgcgtggtg gtggacgtga     900
gccacgaaga ccctgaggtc aagttcaact ggtacgtgga cggcgtggag gtgcataatg     960
ccaagacaaa gccgcgggag gagcagtaca acagcacgta ccgtgtggtc agcgtcctca    1020
ccgtcctgca ccaggactgg ctgaatggca aggagtacaa gtgcaaggtc tccaacaaag    1080
ccctcccagc ccccatcgag aaaaccatct ccaaagccaa agggcagccc cgagaaccac    1140
aggtgtacac cctgccccca tcccgggatg agctgaccaa gaaccaggtc agcctgacct    1200
```

-continued

```
gcctggtcaa aggcttctat cccagcgaca tcgccgtgga gtgggagagc aatgggcagc    1260
cggagaacaa ctacaagacc acgcctcccg tgctggactc cgacggctcc ttcttcctct    1320
atagcaagct caccgtggac aagagcaggt ggcagcaggg gaacgtcttc tcatgctccg    1380
tgatgcatga ggctctgcac aaccactaca cgcagaagag cctctccctg tctccgggta    1440
aatgagcggc cgc                                                       1453
```

<210> SEQ ID NO 2
<211> LENGTH: 458
<212> TYPE: PRT
<213> ORGANISM: Artificial Sequence
<220> FEATURE:
<223> OTHER INFORMATION: Synthetic

<400> SEQUENCE: 2

```
Met Val Ser Tyr Trp Asp Thr Gly Val Leu Leu Cys Ala Leu Leu Ser
  1               5                  10                  15

Cys Leu Leu Leu Thr Gly Ser Ser Ser Gly Gly Arg Pro Phe Val Glu
                 20                  25                  30

Met Tyr Ser Glu Ile Pro Glu Ile Ile His Met Thr Glu Gly Arg Glu
             35                  40                  45

Leu Val Ile Pro Cys Arg Val Thr Ser Pro Asn Ile Thr Val Thr Leu
 50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Val
        115                 120                 125

Leu Ser Pro Ser His Gly Ile Glu Leu Ser Val Gly Glu Lys Leu Val
130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
    210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320
```

```
His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 3
<211> LENGTH: 1377
<212> TYPE: DNA
<213> ORGANISM: Artificial Sequence
<220> FEATURE:
<223> OTHER INFORMATION: Synthetic

<400> SEQUENCE: 3

```
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca cttttgatcc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata gaaacttgt aaaccgagac     540 ctaaaacccc agtctgggag tgagatgaag aaattttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aaagggcagc cccgagaacc acaggtgtac    1080
accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
```

-continued gaggctctgc acaaccacta cacgcagaag agcctctccc tgtctccggg taaatga    1377

<210> SEQ ID NO 4
<211> LENGTH: 458
<212> TYPE: PRT
<213> ORGANISM: Artificial Sequence
<220> FEATURE:
<223> OTHER INFORMATION: Synthetic

<400> SEQUENCE: 4

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu

-continued

```
                355                 360                 365
Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
450                 455
```

STABLE LIQUID VEGF ANTAGONIST FORMULATIONS

CROSS-REFERENCE TO RELATED APPLICATIONS

This application is a continuation of U.S. patent application Ser. No. 13/343,214, filed Jan. 4, 2012, which is a division of U.S. patent application Ser. No. 12/835,065, filed Jul. 13, 2010, and granted as U.S. Pat. No. 8,110,546 on Feb. 7, 2012, which is a continuation of U.S. patent application Ser. No. 11/387,256, filed Mar. 22, 2006, which claims the benefit of priority under 35 USC §119(e) of U.S. Provisional Application No. 60/665,125, filed Mar. 25, 2005, all of which are herein specifically incorporated by reference in their entirety.

BACKGROUND OF THE INVENTION

1. Field of the Invention

The present invention is directed to pharmaceutical formulations comprising agents capable of inhibiting vascular endothelial growth factor (VEGF), and to methods for making and using such formulations. The invention includes pharmaceutical formulations having increased stability.

2. Statement of Related Art

Vascular endothelial growth factor (VEGF) expression is nearly ubiquitous in human cancer, consistent with its role as a key mediator of tumor neoangiogenesis. Blockade of VEGF function, by binding to the molecule or its VEGFR-2 receptor, inhibits growth of implanted tumor cells in multiple different xenograft models (see, for example, Gerber et al. (2000) Cancer Res. 60:6253-6258). A soluble VEGF-specific fusion protein antagonist, termed a "VEGF trap" has been described (Kim et al. (2002) Proc. Natl. Acad. Sci. USA 99:11399-404; Holash et al. (2002) Proc. Natl. Acad. Sci. USA 99:11393-8), which references are specifically incorporated by reference in their entirety.

Lyophilization (freeze drying under controlled conditions) is commonly used for long term storage of proteins. The lyophilized protein is substantially resistant to degradation, aggregation, oxidation, and other degenerative processes while in the freeze-dried state (see, for example, U.S. Pat. No. 6,436,897).

BRIEF SUMMARY OF THE INVENTION

Stable formulations of a VEGF-specific fusion protein antagonist are herein provided. The pharmaceutically acceptable formulations of the invention comprise the VEGF "trap" antagonist with a pharmaceutically acceptable carrier. In specific embodiments, liquid and freeze-dried, or lyophilized formulations are provided.

In a first aspect, the invention features a stable liquid formulation of a VEGF-specific fusion protein antagonist, comprising a fusion protein comprising a receptor component consisting essentially of an immunoglobulin-like (Ig) domain 2 of a first VEGF receptor and Ig domain 3 of a second VEGF receptor, and a multimerizing component, one or more buffers, and one or more thermal stabilizers. In a specific embodiment of the VEGF-specific fusion protein antagonist, the first VEGF receptor is Flt1 and the second VEGF receptor is Flk1 or Flt4. In a more specific embodiment the fusion protein has the amino acid sequence of SEQ ID NO:2 or SEQ ID NO:4. In one embodiment, the buffer is a phosphate buffer and/or citrate. More preferably, the buffers are phosphate and citrate. In one embodiment, the thermal stabilizers are NaCl and/or sucrose. More preferably, the thermal stabilizers are both NaCl and sucrose.

In a specific embodiment, the stable liquid formulation of a VEGF-specific fusion protein antagonist comprises 1-10 mM phosphate buffer, 1-10 mM citrate, 25-150 mM NaCl, 5-30% sucrose, 10-50 mg/ml of the fusion protein, at a pH of about 6-6.5. In a more specific embodiment, the stable liquid formulation comprises 5 mM phosphate buffer, 5 mM citrate buffer, 100 mM NaCl, 20% sucrose, 25 mg/ml of the fusion protein, at a pH of about 6.0. Additionally, polysorbate may be present, for example 0.05-0.15% polysorbate 20. The stable liquid formulation of the VEGF-specific fusion protein antagonist of the invention exhibits little or no precipitation after storage of a 25 mg/ml VEGF formulation for about 6 months at −80° C. and little or no precipitation after storage for 6 months at 5° C.

In a second aspect, the invention features a high concentration stable liquid formulation of a VEGF antagonist comprising 1-50 mM histidine, 25-150 mM NaCl, 5-30% sucrose, 50-100 mg/ml of the fusion protein, at a pH of about 6-6.5, and either 0.1-0.5% polysorbate or 1-5% PEG. In a more specific embodiment, the high concentration stable liquid formulation comprises 10 mM histidine, 50 mM NaCl, 5-20% sucrose, 50-100 mg/ml of the fusion protein, at a pH of about 6.0-6.5, with either 0.1% polysorbate (e.g., polysorbate 20) or 3% PEG (e.g., PEG 3350). The high concentration stable liquid formulation of the VEGF-specific fusion protein antagonist of the invention exhibits less than about 3% degradation after 15 months of storage at 5° C. (75 or 100 mg/ml VEGF trap protein) or less than about 1.5% degradation after 24 months (50 mg/ml).

In a third aspect, the invention features a pre-lyophilized formulation of a vascular endothelial growth factor (VEGF)-specific fusion protein antagonist, comprising a (i) fusion protein comprising a receptor component consisting essentially of an immunoglobulin-like (Ig) domain 2 of a first VEGF receptor and Ig domain 3 of a second VEGF receptor, and a multimerizing component, (ii) a buffer, (iii) an organic co-solvent or bulking agent, and (iv) one or more lyoprotectants. In various embodiments, the buffer is histidine, the organic co-solvent or bulking agent is PEG, and the lyoprotectant(s) is at least one of glycine and sucrose. In one embodiment, the pre-lyophilized formulation of the invention does not contain a preservative.

In one embodiment of the pre-lyophilized formulation of the invention, the formulation comprises 5-50 mM histidine, 0.1-3.0% PEG, 0.25-3.0% glycine, 0.5-6.0% sucrose, and 5-75 mg/ml of the fusion protein, at a pH of about 6.0-6.5. In any embodiment, the pre-lyophilized formulation may further comprise up to 0.05 mM citrate and/or 0.003-0.005% polysorbate. The polysorbate present may be, for example, polysorbate 20.

In a more specific embodiment, the pre-lyophilized formulation comprises about 10 mM histidine, about 1.5% PEG 3350, about 0.75% glycine, about 2.5% sucrose, and about 12.5 to 75 mg/ml VEGF-specific fusion protein, at a pH of about 6.25. In specific embodiments, the fusion protein comprises the protein sequence of SEQ ID NO:4, present as a multimer, e.g., a dimer. In separate embodiments, the reconstituted formulation is 2 times the concentration of the pre-lyophilized formulation, e.g., a 20 mg fusion protein/ml pre-lyophilized formulation is reconstituted to a final formulation of 60 mg fusion protein/ml. Generally, the lyophilized formulation is reconstituted with sterile water suitable for injection. In one embodiment, the reconstitution liquid may be bacteriostatic water.

In a preferred embodiment, the pre-lyophilized formulation consists essentially of about 10 mM histidine, about 1.5% PEG 3350, about 0.75% glycine, about 2.5% sucrose, and about 50 mg/ml of the fusion protein having the sequence of SEQ ID NO:4 as a dimer, at a pH of about 6.25. Citrate (less than or equal to about 0.02 mM) and/or polysorbate (less than or equal to about 0.0005%) may be present. Optionally, the pre-lyophilized formulation does not contain a preservative, a phosphate buffer, and/or more than trace amounts of NaCl. In one embodiment, the pre-lyophilized formulation consists of about 10 mM histidine, about 1.5% PEG 3350, about 0.75% glycine, about 2.5% sucrose, and about 50 mg/ml of the VEGF trap protein (SEQ ID NO:4), pH 6.3, and upon reconstitution contains 20 mM histidine, 3% PEG, 1.5% glycine, about 5% sucrose, and about 100 mg/ml VEGF trap protein.

In a fourth aspect, the invention features a method of producing a lyophilized formulation of a VEGF-specific fusion protein antagonist, comprising subjecting the pre-lyophilized formulation of the invention to lyophilization to generate a lyophilized formulation. The lyophilized formulation may be lyophilized by any method known in the art for lyophilizing a liquid.

In a fifth related aspect, the invention features a method of producing a reconstituted lyophilized formulation of a VEGF-specific fusion protein antagonist, comprising reconstituting the lyophilized formulation of the invention to a reconstituted formulation. In one embodiment, the reconstituted formulation is twice the concentration of the pre-lyophilized formulation, e.g., the method of the invention comprises: (a) producing a pre-lyophilized formulation of a VEGF-specific fusion protein antagonist, (b) subjecting the pre-lyophilized formulation of step (a) to lyophilization; and (c) reconstituting the lyophilized formulation of step (b).

In specific embodiments of the method of producing a reconstituted lyophilized formulation, a pre-lyophilized solution is present in a vial as a 25 mg VEGF-specific fusion protein antagonist per ml solution of pre-lyophilized formulation, which is lyophilized and reconstituted to an 50 mg/ml solution. In another embodiment, a 30 mg/ml pre-lyophilized solution is lyophilized and reconstituted to a 60 mg/ml solution. In another embodiment, a 40 mg/ml pre-lyophilized solution is lyophilized and reconstituted to a 80 mg/ml solution. In another embodiment, a 12.5 mg/ml pre-lyophilized solution is lyophilized and reconstituted to a 25 mg/ml solution. In another embodiment, a 50 mg/ml pre-lyophilized solution is lyophilized and reconstituted to a 100 mg/ml solution. In another embodiment, a 75 mg/ml pre-lyophilized solution is lyophilized and reconstituted to a 150 mg/ml solution. Preferably, the reconstituted lyophilized formulation does not contain a preservative.

Other objects and advantages will become apparent from a review of the ensuing detailed description.

DETAILED DESCRIPTION OF THE INVENTION

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure.

Unless stated otherwise, all technical and scientific terms and phrases used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference.

General Description

Safe handling and administration of formulations comprising proteins represent significant challenges to pharmaceutical formulators. Proteins possess unique chemical and physical properties that present stability problems: a variety of degradation pathways exist for proteins, implicating both chemical and physical instability. Chemical instability includes deamination, aggregation, clipping of the peptide backbone, and oxidation of methionine residues. Physical instability encompasses many phenomena, including, for example, aggregation.

Chemical and physical stability can be promoted by removing water from the protein. Lyophilization (freeze-drying under controlled conditions) is commonly used for long-term storage of proteins. The lyophilized protein is substantially resistant to degradation, aggregation, oxidation, and other degenerative processes while in the freeze-dried state. The lyophilized protein is normally reconstituted with water optionally containing a bacteriostatic preservative (e.g., benzyl alcohol) prior to administration.

DEFINITIONS

The term "carrier" includes a diluent, adjuvant, excipient, or vehicle with which a composition is administered. Carriers can include sterile liquids, such as, for example, water and oils, including oils of petroleum, animal, vegetable or synthetic origin, such as, for example, peanut oil, soybean oil, mineral oil, sesame oil and the like.

The term "excipient" includes a non-therapeutic agent added to a pharmaceutical composition to provide a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "lyophilized" or "freeze-dried" includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Generally, acceptable bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen, and synthetic monomers and polymers. In the formulations of the invention, PEG 3350 is an organic co-solvent which is used to stabilize the fusion protein when agitated, mixed, or handled, and as a bulking agent to help produce an acceptable bulk.

The term "lyoprotectant" includes a substance that may be added to a freeze-dried or lyophilized formulation to help maintain protein structure when freeze-dried or lyophilized.

A "preservative" includes a bacteriostatic, bacteriocidal, fungistatic or fungicidal compound that is generally added to formulations to retard or eliminate growth of bacteria or other contaminating microorganisms in the formulations. Preservatives include, for example, benzyl alcohol, phenol, benzalkonium chloride, m-cresol, thimerosol, chlorobutanol, methylparaben, propylparaben and the like. Other examples of pharmaceutically acceptable preservatives can be found in the USP.

VEGF Antagonists

An VEGF antagonist is a compound capable of blocking or inhibiting the biological action of vascular endothelial growth factor (VEGF), and includes fusion proteins capable of trapping VEGF. In a preferred embodiment, the VEGF antagonist is the fusion protein of SEQ ID NO:2 or 4; more preferably, SEQ ID NO:4. In specific embodiments, the VEGF antagonist is expressed in a mammalian cell line such as a CHO cell and may be modified post-translationally. In a specific embodiment, the fusion protein comprises amino acids 27-457 of SEQ ID NO:4 and is glycosylated at Asn residues 62, 94, 149, 222 and 308.

The VEGF antagonist of the methods and formulations of the invention can be prepared by any suitable method known in the art, or that comes to be known. The VEGF antagonist is preferably substantially free of protein contaminants at the time it is used to prepare the pharmaceutically acceptable formulation. By "substantially free of protein contaminants" is meant, preferably, that at least 90% of the weight of protein of the VEGF-specific fusion protein antagonist preparation used for making a formulation is VEGF fusion protein antagonist protein, more preferably at least 95%, most preferably at least 99%. The fusion protein is preferably substantially free of aggregates. "Substantially free of aggregates" means that at least 90% of the weight of fusion protein is not present in an aggregate at the time the fusion protein is used to prepare the pharmaceutically effective formulation. The fusion protein of the methods and formulations of the invention may contain low or trace amounts of compounds as a results of the purification process, for example, low or trace amounts of citrate and/or polysorbate. In one embodiment of the pre-lyophilized formulation of the invention containing about 50 mg of fusion protein/ml, citrate may be present at a concentration of about 0.02 mM and/or polysorbate may be present at a concentration of about 0.0005%. If the pre-lyophilized formulation is reconstituted after lyophilization to half of the original volume (e.g., 100 mg/ml of fusion protein), the resulting concentrations may be 0.04 mM citrate and/or 0.001% polysorbate.

Lyophilization and Lyophilized Formulations

In one aspect of the invention, a pharmaceutically acceptable formulation comprising a VEGF-specific fusion protein antagonist is provided, wherein the formulation is a freeze-dried or lyophilized formulation. Lyophilized formulations can be reconstituted into solutions, suspensions, emulsions, or any other suitable form for administration or use. Lyophilized formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored below 25° C., for example, refrigerated at 4° C., or at room temperature (e.g., approximately 25° C.). Preferably, lyophilized formulations are stored below about 25° C., more preferably, at about 4-20° C.; below about 4° C.; below about −20° C.; about −40° C.; about −70° C., or about −80° C.

Lyophilized formulations are typically reconstituted for use by addition of an aqueous solution to dissolve the lyophilized formulation. A wide variety of aqueous solutions can be used to reconstitute a lyophilized formulation. Preferably, lyophilized formulations are reconstituted using water. Lyophilized formulations are preferably reconstituted with a solution consisting essentially of water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used.

Freeze-dried or lyophilized formulations are typically prepared from liquids, that is, from solutions, suspensions, emulsions, and the like. Thus, the liquid that is to undergo freeze-drying or lyophilization preferably comprises all components desired in a final reconstituted liquid formulation. As a result, when reconstituted, the freeze-dried or lyophilized formulation will render a desired liquid formulation upon reconstitution. A preferred liquid formulation used to generate a freeze-dried or lyophilized formulation comprises a VEGF-specific fusion protein antagonist in a pharmaceutically effective amount, a buffer, a stabilizer, and a bulking agent. Freeze-dried or lyophilized formulations preferably comprise histidine, since histidine, in comparison to phosphate, is more effective at stabilizing the fusion protein when the fusion protein is lyophilized. Organic co-solvents, such as PEG 3350, are used to stabilize the fusion protein when agitated, mixed, or handled. A lyoprotectant is preferably used in freeze-dried or lyophilized formulations. Lyoprotectants help to maintain the secondary structure of proteins when freeze-dried or lyophilized. Two preferred example lyoprotectants are glycine and sucrose, which are preferably used together.

Stable Liquid Formulations

In one aspect, the invention provides a stable pharmaceutically acceptable formulation comprising a VEGF-specific fusion protein antagonist, wherein the formulation is a liquid formulation. Preferably, the liquid formulation comprises a pharmaceutically effective amount of the fusion protein. The formulation can also comprise one or more pharmaceutically acceptable carriers, buffers, bulking agents, stabilizers, preservatives, and/or excipients. An example of a pharmaceutically acceptable liquid formulation comprises a VEGF-specific fusion protein antagonist in a pharmaceutically effective amount, a buffer, a co-solvent, and one or more stabilizers.

A preferred liquid formulation comprises phosphate buffer, an organic co-solvent, and one or more thermal stabilizers to minimize formation of aggregates and low molecular weight products when stored, and about 10 mg/ml to about 50 mg/ml fusion protein, wherein the formulation is from about pH 6.0-6.5. A preferred liquid formulation comprises about 5 mM phosphate buffer, about 5 mM citrate, about 100 mM NaCl, about 25% sucrose, and about 10-50 mg/ml fusion protein, wherein the formulation is at a pH of about 6.0; optionally polysorbate may be present (e.g., 0.1% polysorbate 20). Although either NaCl or sucrose can be used as a stabilizer, a combination of NaCl and sucrose has been established to stabilize the fusion protein more effectively than either individual stabilizer alone.

Stability is determined in a number of ways at specified time points, including determination of pH, visual inspection of color and appearance, determination of total protein content by methods known in the art, e.g., UV spectroscopy, SDS-PAGE, size-exclusion HPLC, bioassay determination of activity, isoelectric focusing, and isoaspartate quantification. In one example of a bioassay useful for determining VEGF antagonist activity, a BAF/3 VEGFR1/EPOR cell line is used to determine VEGF165 binding by the VEGF-specific fusion protein antagonist of the invention.

Formulations, whether liquid or freeze-dried and lyophilized, can be stored in an oxygen-deprived environment. Oxygen-deprived environments can be generated by storing the formulations under an inert gas such as, for example, argon, nitrogen, or helium.

EXAMPLES

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only to the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

Example 1

Stability of a 50 mg/ml Liquid Formulation of VEGF Trap

A liquid formulation containing 10 mM phosphate, 50 mM NaCl, 0.1% polysorbate 20, 20% sucrose, and 50 mg/ml VEGF trap (SEQ ID NO:4), pH 6.25, was stored at 5° C. and samples tested at 3, 6, 9, 12, 18 and 24 months. Stability was determined by SE-HPLC. The results, shown in Table 1, show that 98.6% and 98.3% of VEGF trap protein remained intact (non-degraded) at 12 and 24 months, respectively. Turbidity was measured at $OD_{405}$ nm; and percent recovered protein by size exclusion HPLC.

TABLE 1

Stability of 50 mg/ml VEGF Trap Protein When Stored at 5° C. (VGFT-SS065)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 99.0 |
| 3 | Pass | 0.00 | 6.2 | 102 | 98.8 |
| 6 | Pass | 0.01 | 6.2 | 103 | 98.7 |
| 9 | Pass | 0.01 | 6.3 | 102 | 98.2 |
| 12 | Pass | 0.01 | 6.3 | 106 | 98.6 |
| 18 | Pass | 0.00 | 6.3 | 103 | 98.4 |
| 24 | Pass | 0.00 | 6.2 | 93 | 98.3 |

A liquid formulation containing 10 mM phosphate, 50 mM NaCl, 3% PEG 3350, 20% sucrose, and 50 mg/ml VEGF trap (SEQ ID NO:4), pH 6.25, was stored at 5° C. and samples tested at 3, 6, 9, 12, 18 and 24 months. Stability results are shown in Table 2.

TABLE 2

Stability of 50 mg/ml VEGF Trap Protein When Stored at 5° C. (VGFT-SS065)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 99.0 |
| 3 | Pass | 0.00 | 6.2 | 100 | 98.8 |
| 6 | Pass | 0.01 | 6.3 | 103 | 98.5 |
| 9 | Pass | 0.00 | 6.3 | 103 | 98.3 |
| 12 | Pass | 0.01 | 6.3 | 110 | 98.3 |
| 18 | Pass | 0.00 | 6.3 | 113 | 98.0 |
| 24 | Pass | 0.01 | 6.2 | 90 | 97.8 |

Example 2

Stability of a 75 mg/ml Liquid Formulation of VEGF Trap

A liquid formulation containing 10 mM phosphate, 50 mM NaCl, 0.1% polysorbate 20, 20% sucrose, and 75 mg/ml VEGF trap (SEQ ID NO:4), pH 6.25, was stored at 5° C. and samples tested at 0, 1, 2.3, 3, 9, 12 and 15 months. Stability results are shown in Table 3.

TABLE 3

Stability of 75 mg/ml VEGF Trap Protein When Stored at 5° C. (VGFT-SS101)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 97.1 |
| 1 | Pass | 0.00 | 6.2 | 96 | 97.0 |
| 2.3 | Pass | 0.00 | 6.2 | 98 | 96.7 |
| 3 | Pass | 0.00 | 6.2 | 97 | 96.1 |
| 9 | Pass | −0.01 | 6.0 | 101 | 96.0 |
| 12 | Pass | 0.00 | 6.3 | 110 | 94.5 |
| 15 | Pass | 0.00 | 6.3 | 92 | 95.6 |

A liquid formulation containing 10 mM phosphate, 50 mM NaCl, 3% PEG 3350, 20% sucrose, and 75 mg/ml VEGF trap (SEQ ID NO:4), pH 6.25, was stored at 5° C. and samples tested at 0, 1, 2.3, 3, 9, 12 and 15 months. Stability results are shown in Table 4.

TABLE 4

Stability of 75 mg/ml VEGF Trap Protein When Stored at 5° C. (VGFT-SS101)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 96.8 |
| 1 | Pass | 0.00 | 6.2 | 99 | 96.7 |
| 2.3 | Pass | 0.00 | 6.2 | 97 | 96.3 |
| 3 | Pass | 0.00 | 6.2 | 89 | 95.6 |
| 9 | Pass | −0.01 | 6.2 | 98 | 95.4 |
| 12 | Pass | −0.01 | 6.3 | 112 | 94.1 |
| 15 | Pass | 0.00 | 6.3 | 98 | 94.8 |

Example 3

Stability of a 100 mg/ml Liquid Formulation of VEGF Trap

A liquid formulation containing 10 mM phosphate, 50 mM NaCl, 0.1% polysorbate 20, 20% sucrose, and 100 mg/ml VEGF trap (SEQ ID NO:4), pH 6.25, was stored at 5° C. and samples tested at 0, 1, 2.3, 3, 9, 12 and 15 months. Stability results are shown in Table 5.

TABLE 5

Stability of 100 mg/ml VEGF Trap Protein Stored at 5° C. (VGFT-SS101)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 96.7 |
| 1 | Pass | 0.00 | 6.2 | 92 | 96.6 |
| 2.3 | Pass | 0.00 | 6.2 | 92 | 96.2 |
| 6 | Pass | 0.00 | 6.2 | 99 | 95.5 |
| 9 | Pass | −0.01 | 6.2 | 92 | 95.5 |
| 12 | Pass | −0.01 | 6.2 | 110 | 93.9 |
| 15 | Pass | 0.00 | 6.3 | 108 | 94.8 |

A liquid formulation containing 10 mM phosphate, 50 mM NaCl, 3% PEG 3350, 20% sucrose, and 100 mg/ml VEGF trap (SEQ ID NO:4), pH 6.25, was stored at 5° C. and samples tested at 0, 1, 2.3, 3, 9, 12 and 15 months. Stability results are shown in Table 6.

TABLE 6

Stability of 100 mg/ml VEGF Trap Protein Stored at 5° C. (VGFT-SS101)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 96.5 |
| 1 | Pass | 0.01 | 6.2 | 94 | 96.2 |
| 2.3 | Pass | 0.01 | 6.2 | 93 | 95.7 |
| 6 | Pass | 0.01 | 6.2 | 102 | 94.6 |
| 9 | Pass | 0.00 | 6.2 | 95 | 94.6 |
| 12 | Pass | 0.00 | 6.3 | 96 | 92.8 |
| 15 | Pass | 0.01 | 6.3 | 102 | 93.9 |

Example 4

Further Embodiments of Stable VEGF Trap Formulations

In one embodiment, the invention provides a stable liquid VEGF-binding fusion protein (VEGF trap) formulations comprising 5 mM phosphate, 5 mM citrate, 100 mM NaCl, 0.1% Polysorbate 20, 20% sucrose, 25 mg/ml VEGF trap protein, pH 6.0. This formulation can either be delivered subcutaneously or diluted and delivered by intravenous infusion. Due to the high osmolality of this formulation, it is diluted 3-fold to achieve an iso-osmolar solution for intravenous administration. Stability studies showed less than about 1% degradation was detected after 3 years of storage at 2-8° C.

In one embodiment, the invention features a lyophilized formulation which is preferably concentrated two-fold from the pre-lyophilized to the post-lyophilized formulation, e.g., 50 to 100 mg/ml; 75 to 150 mg/ml, or 100 to 200 mg/ml VEGF trap protein. In one specific embodiment, the pre-lyophilized formulation comprises 10 mM histidine, 1.5% PEG 3350, 0.75% glycine, 2.5% sucrose, 50 mg/ml VEGF trap protein, pH 6.3, and is reconstituted to a formulation comprising 20 mM histidine, 3% PEG 3350, 1.5% glycine, 5% sucrose, 100 mg/ml VEGF trap protein, pH 6.3. Stability studied showed no degradation of the VEGF trap was detected after 6 months of storage at 2-8° C.

In one embodiment of a liquid formulation, the formulation comprises 10 mM histidine, 50 mM NaCl, 5-20% sucrose, 50-100 mg/ml VEGF trap, and one of 0.1% polysorbate 20 or 3° PEG 3350. One advantage of this liquid formulation is that it provides a higher concentration of VEGF trap without requiring the manufacture of a lyophilized product. Thus, this formulation provides ease for subcutaneous delivery, for example, by allowing provision of a liquid pre-filled syringe at a concentration higher than that delivered by IV infusion. Also, this formulation could advantageously be used to provide lower infusion volumes and shorter infusion times. The amount of degradation determined by SE-HPLC following incubation at 5° C. for up to 15 or 24 months is summarized in Table 7.

TABLE 7

Stability of Liquid Formulation with 50-100 mg/ml VEGF Trap (VGFT-SS101)

| Incubation (months) | VEGF Trap (mg/ml) | % Polysorbate 20 | % PEG 3350 | % Degradation |
|---|---|---|---|---|
| 24 | 50 | 0.1 | — | 0.7 |
| 24 | 50 | — | 3 | 1.3 |
| 15 | 75 | 0.1 | — | 1.5 |
| 15 | 75 | — | 3 | 2.0 |
| 15 | 100 | 0.1 | — | 1.9 |
| 15 | 100 | — | 3 | 2.6 |

Example 5

Stability and Activity of Lyophilized and Liquid

The stability of a reconstituted lyophilized formulation was determined over a 6 month period. The pre-lyophilized formulation contained 10 mM histidine, 1.5% PEG 3350, 2.5% sucrose, 0.75% glycine and 50 mg/ml VEGF trap protein. After lyophilization, the reconstituted formulation contained 20 mM histidine, 3% PEG 3350, 5% sucrose, 1.5% glycine, and 100 mg/ml VEGF trap protein (SEQ ID NO:4). The results shown in Table 8. Activity was determined in a cell based bioassay which directly measures the ability of the VEGF trap to inhibit the biological effects of human VEGF on a mouse Baf/3 VEGFR1/EpoR cell line. Therefore, this bioassay directly measures the biological activity of the protein. The results are expresses as percent relative potency (test sample $IC_{50}$/reference VEGF $IC_{50}$ standard×100). The binding affinity of VEGF to the VEGF trap is measured using a sensitive ELISA that specifically measures free VEGF in equilibrated mixtures containing VEGF and various concentrations of the VEGF trap. Results are expressed as percent relative binding ($IC_{50}$ of test sample/$IC_{50}$ of reference×100). Measured pH ranged between 6.3-6.5. All solutions where visually clear. The concentration of VEGF trap recovered was determined with a UV spectrophotometer as mg/ml at $A_{280}$ nm. The percent VEGF trap recovered in the native configuration (main peak purity) was determined with SE-HPLC.

TABLE 8

Stability of VEGF Trap Lyophilized Formulation Stored at 5° C. (VGT-RS475)

| Months | Bioassay | Binding Assay | % Recovered | % Native Configuration |
|---|---|---|---|---|
| 0 | 120 | 126 | 97.9 | 98.7 |
| 1 | 117 | 74 | 97.9 | 98.6 |
| 1 + 24 hr | 126 | 72 | 99.0 | 98.5 |
| 1 + 4 hr | 94 | 81 | 101.5 | 98.2 |
| 3 | 101 | 98 | 98.1 | 98.6 |
| 3 + 24 hr | 65 | 94 | 98.1 | 98.2 |
| 6 + 4 hr | | | 96.9 | 98.7 |
| 6 + 24 hr | | | 98.8 | 98.6 |

A formulation containing about 5 mM phosphate, 5 mM citrate, 100 mM NaCl, 0.1% polysorbate 20, 20% sucrose, and 25 mg/ml VEGF trap protein was tested for stability and activity over 36 months when stored at 5° C. The results are shown in Table 9. All samples were clear and colorless as determined by visual inspection. pH ranged from 6.0-6.1. *Binding assay results for two measurements (1 and 2 months) are expressed directly and not as a percent of the standard.

TABLE 9

Stability and Activity of Liquid Formulation (VGT-FS405)

| Months | % Native Configuration | Bioassay | Binding Assay | Protein Content mg/ml |
|---|---|---|---|---|
| 0 | 99.7 | 106 | 72 | 25.0 |
| 1 | 99.9 | 119 | 4.4 pM* | 25.2 |
| 2 | 99.6 | 102 | 5.4 pM* | 25.1 |
| 3 | 99.6 | 97 | 88 | 25.1 |
| 6 | 99.6 | 101 | 106 | 25.0 |
| 9 | 99.4 | 89 | 126 | 25.4 |
| 12 | 99.5 | 85 | 95 | 25.2 |
| 18 | 99.4 | 99 | 81 | 25.5 |
| 24 | 99.3 | 75 | 95 | 25.6 |
| 36 | 98.8 | 109 | 79 | 25.6 |

We claim:

1. A stable liquid formulation of a vascular endothelial growth factor (VEGF)-specific fusion protein antagonist, comprising 10-100 mg/ml of a fusion protein comprising amino acids 27-457 of SEQ ID NO: 4; 5 mM phosphate and 5 mM citrate, at a pH of about 6.0-6.5; about 20% sucrose; about 50-100 mM NaCl; and about 0.1% polysorbate 20.

2. The stable liquid formulation of claim 1, wherein about 99% of the fusion protein antagonist is undegraded following storage at 5° C. for 24 months, and wherein the fusion protein displays about 75-100% of maximal potency in a bioassay in a mouse 8af/3 VEGFR1/EpoR cell line.

3. The stable liquid formulation of claim 1, comprising 25-50 mg/ml of the fusion protein.

4. The stable liquid formulation of claim 1, comprising 5 mM phosphate buffer, 5 mM citrate buffer, 100 mM NaCl, 20% sucrose, 0.1% polysorbate 20, and 50 mg/ml of the fusion protein, at a pH of about 6.0.

5. The stable liquid formulation of claim 4, consisting essentially of 5 mM phosphate buffer, 5 mM citrate buffer, 100 mM NaCl, 20% sucrose, 0.1% polysorbate 20, and 50 mg/ml of the fusion protein, in water for injection, at a pH of about 6.0.

6. The stable liquid formulation of claim 1, wherein at least 92% of the fusion protein antagonist is present in native conformation as measured by SE-HPLC following storage at 5° C. for 12 months.

* * * * *